(12) United States Patent
Okitsu et al.

(10) Patent No.: US 12,740,978 B2
(45) Date of Patent: Sep. 22, 2026

(54) TLR7/8 ANTAGONISTS AND USES THEREOF

(71) Applicant: Merck Patent GmbH, Darmstadt (DE)

(72) Inventors: Lukas Shinji Okitsu, Billerica, MA (US); Julie DeMartino, Billerica, MA (US); Thomas Spangenberg, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 541 days.

(21) Appl. No.: 18/001,775

(22) PCT Filed: Jun. 1, 2021

(86) PCT No.: PCT/US2021/035174
§ 371 (c)(1),
(2) Date: Dec. 14, 2022

(87) PCT Pub. No.: WO2021/257273
PCT Pub. Date: Dec. 23, 2021

(65) Prior Publication Data

US 2023/0301981 A1 Sep. 28, 2023

Related U.S. Application Data

(60) Provisional application No. 63/039,142, filed on Jun. 15, 2020.

(51) Int. Cl.
*A61K 31/4706* (2006.01)
*A61K 31/4745* (2006.01)
(Continued)

(52) U.S. Cl.
CPC ...... *A61K 31/4706* (2013.01); *A61K 31/4745* (2013.01); *A61K 31/675* (2013.01); *A61K 45/06* (2013.01); *A61P 37/02* (2018.01)

(58) Field of Classification Search
CPC ........... A61K 31/4706; A61K 31/4745; A61K 31/675; A61K 45/06; A61P 37/02
See application file for complete search history.

(56) References Cited

U.S. PATENT DOCUMENTS 11,696,914 B1 7/2023 Ekins et al.
2006/0035929 A1* 2/2006 Giulian et al. ......... A61K 45/06 514/311
(Continued)

FOREIGN PATENT DOCUMENTS

CN 1809357 B 12/2010
JP 2013075834 A 4/2013
(Continued)

OTHER PUBLICATIONS

Cynthia Liu, Qiongqiong Zhou, Yingzhu Li, Linda V. Garner, Steve P. Watkins, Linda J. Carter, Jeffrey Smoot, Anne C. Gregg, Angela D. Daniels, Susan Jervey, and Dana Albaiu ACS Central Science 2020 6 (3), 315-331 DOI: 10.1021/acscentsci.0c00272 (Year: 2020).*
(Continued)

*Primary Examiner* — Rachael E Bredefeld
(74) *Attorney, Agent, or Firm* — Fox Rothschild LLP

(57) ABSTRACT

Compounds disclosed herein and pharmaceutically acceptable compositions thereof are useful as TLR7/8 antagonists.

13 Claims, 4 Drawing Sheets

(51) Int. Cl.

| | |
|---|---|
| ***A61K 31/675*** | (2006.01) |
| ***A61K 45/06*** | (2006.01) |
| ***A61P 37/02*** | (2006.01) |

(56) References Cited

U.S. PATENT DOCUMENTS

| | | | |
|---|---|---|---|
| 2015/0148377 | A1 | 5/2015 | Hogenauer et al. |
| 2017/0174653 | A1 | 6/2017 | Sherer et al. |

FOREIGN PATENT DOCUMENTS

| | | | | | |
|---|---|---|---|---|---|
| JP | 2017533925 | A | 11/2017 | | |
| WO | 2016075661 | A1 | 5/2016 | | |
| WO | WO-2019018354 | A1 * | 1/2019 | ........... | C07D 401/10 |
| WO | 2019/197367 | | 10/2019 | | |
| ZA | 200510028 | B | 3/2007 | | |

OTHER PUBLICATIONS

Colson et al., "Chloroquine and hydroxychloroquine as available weapons to fight Covid-19", International Journal of Antimicrobial Agents, vol. 55, 2020, 105932, pp. 1-3.
International Search Report dated Sep. 16, 2021, in PCT/US2021/035174, 5 pages.
Kandimalla et al., "Design, synthesis and biological evaluation of novel antagonist compounds of Toll-like receptors 7, 8 and 9", Nucleic Acids Research, vol. 41, No. 6, Feb. 8, 2013, pp. 3947-3961.
Puhl et al., "Repurposing the Ebola and Marburg Virus Inhibitors Tilorone, Quinacrine, and Pyronaridine: In Vitro Activity against SARS-CoV-2 and Potential Mechanisms" ACS Omega 2021, vol. 6, 2021, pp. 7454-7468.
Rainsford et al.," Therapy and pharmacological properties of hydroxychloroquine and chloroquine in treatment of systemic lupus erythematosus, rheumatoid arthritis and related diseases", Inflammopharmacology, vol. 23, 2015, pp. 231-269.
Relations Media et al., "Merck KGaA, Darmstadt, Germany, Initiates First Clinical Trial of TLR7 and 8 Inhibitor as a Potential Treatment for Severe Symptoms of Covid-19 Infection", Jun. 25, 2020, 3 pages.
Wen-Chien et al., "Arguments in favour of remdesivir for treating SARS-CoV-2 infections", International Journal of Antimicrobial Agents, vol. 55, 2020, 105933, pp. 1-3.
Written Opinion dated Sep. 16, 2021, in PCT/US2021/035174, 7 pages.
Lane, T. R. et al., "Repurposing the Antimalarial Pyronaridine Tetraphosphate to Protect against Ebola Virus Infection", PLOS-One (2019), vol. 13:11, e0007890 (16 pgs).
Jeon, S. et al., "Identification of Antiviral Drug Candidates against SARS-CoV-2 from FDA-Approved Drugs", Mar. 20, 2020, retrieve on Apr. 11, 2025, from URL: https: //www.biorxiv.org/content/10.1101/2020. 03.20.999730v1; 21 pgs.

* cited by examiner

TLR7/8 ANTAGONISTS AND USES THEREOF

CROSS-REFERENCE TO RELATED APPLICATIONS

This application is the National Stage entry under § 371 of International Application No. PCT/US2021/035174, filed on Jun. 1, 2021, and which claims the benefit of priority to U.S. Provisional Application No. 63/039,142, filed on Jun. 15, 2020. The content of each of these applications is hereby incorporated by reference in its entirety.

BACKGROUND OF THE INVENTION

Field of the Invention

The present invention provides for compounds of Formula (I) as toll-like receptor 7/8 (TLR7/8) antagonists and their use in the treatment of immune disorders, and other diseases related to TLR7/8 overexpression.

Description of Related Art

Toll-like receptors (TLR) currently comprising a gene family of 10 receptors with different specificities are part of the cellular pathogen pattern recognition system, which has evolved for defense against a variety of infections (bacteria, virus, fungi). Activation of TLRs leads to cytokine responses, e.g. with release of interferons and activation of specified immune cells. The functional expression of selected TLRs in tissues is highly different. Part of the receptors are located at the cell surface such as TLR4 (stimulated by *E. coli* lipopolysaccharide LPS), e.g. on epithelial cells, or TLR3, 7, 8 and 9 located at endosomal membranes in specified immune cells. The latter are all activated by nucleic acids but recognize various types of them. For instance, TLR9 is activated by single stranded DNA containing CpG subsequences, TLR7 and 8 are activated by single stranded RNA, and TLR3 is activated by double-stranded RNA.

TLRs have been implicated in various autoimmune and inflammatory diseases, with the clearest example being the role played by TLR7 in the pathogenesis of systemic lupus erythematosus (Barrat and Coffman, Immunol Rev, 223: 271-283, 2008). Additionally, a TLR8 polymorphism has been associated with rheumatoid arthritis (Enevold et al., J Rheumatol, 37:905-10, 2010). Although various TLR7, TLR8 and TLR9 inhibitors have been described, additional TLR inhibitors are desirable. In particular, polynucleotides having inhibitory motifs for one or more of TLR7, TLR8 and TLR9 are needed to precisely inhibit an immune response in a subject (e.g., patient having an autoimmune disease or an inflammatory disorder).

For several years strong efforts are ongoing worldwide trying to exploit the strong immune activation induced by TLR7, 8 or 9 agonists for the treatment of cancer. Cancer immunotherapy, however, experienced a long history of failures. In recent years, though, the knowledge on cancer immune surveillance and the function of subsets of immune cells thereby was improved drastically. TLR7 or TLR9 agonists are in clinical development for cancer mono- or combination therapies, or as vaccine adjuvant. The TLR agonist approach for cancer immunotherapy is different from earlier efforts using, e.g. cytokines, interferons or monovalent vaccinations. TLR agonist mediated immune activation is pleiotropic via specified immune cells (primarily dendritic cells and B-cells, subsequently other cells), which generates an innate and adaptive immune response. Moreover, not only one interferon is induced, but rather the many different isoform's altogether, and not only type I (alpha, beta), but also (indirectly) type II (gamma, NK cells).

SUMMARY OF THE INVENTION

In one aspect, the invention provides a compound selected from the group consisting of:

(I)

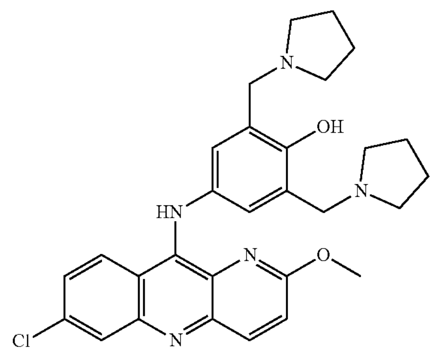

Pyronaridine (II)

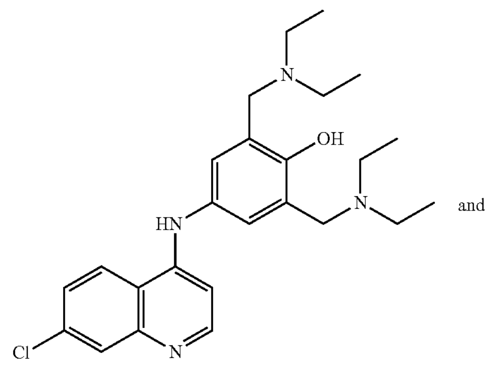

and

Cycloquine (III)

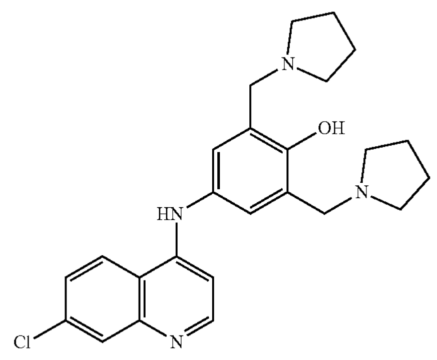

Bispyroquine and/or a pharmaceutically acceptable salt thereof.

In another aspect, the invention provides a compound of the invention which is a dual antagonist of TLR7 and TLR8. In another aspect, the invention provides a compound of the invention which is suitable for the treatment and/or prevention of disorders related to TLR7/8. In another aspect, the invention provides a compound which is able to modulate, especially inhibit the activity or function of TLR7/8 in disease states in mammals, especially in humans.

According to another aspect of the invention are provided methods for the treatment and/or prevention of auto-immune disorders.

According to another aspect, the present invention provides a compound as shown above which is selective for TLR7 or TLR8.

According to another aspect, the present invention provides a compound of the invention which is selective for TLR7 and TLR8.

DETAILED DESCRIPTION OF THE INVENTION

Figure 1:
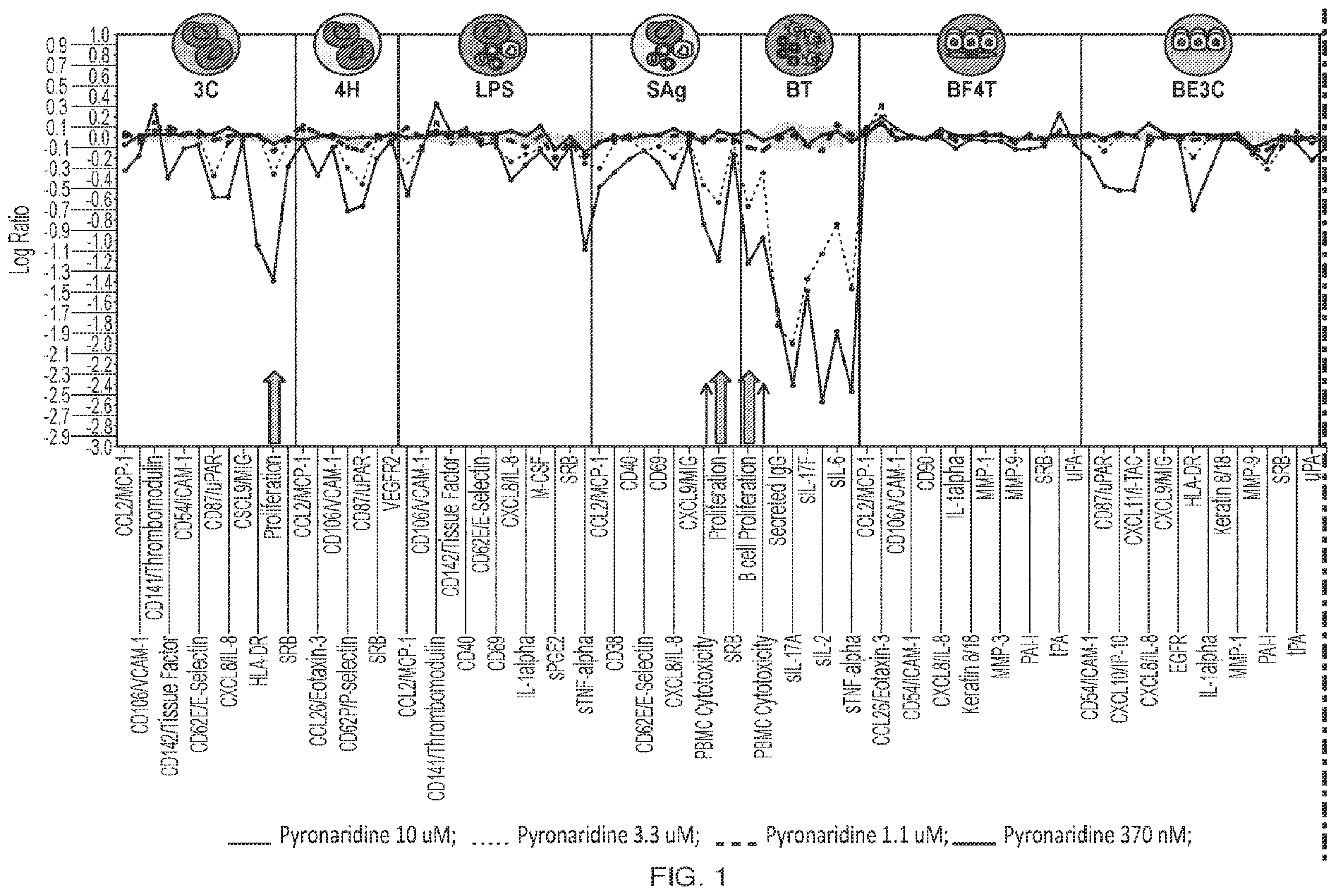
FIG. 1 shows the profile of Pyronaridine in the BioMAP® Diversity PLUS panel at 10, 3.3, 1.1, and 0.3 μM. The latter system models the T cell dependent B cell proliferation, activation and class switching that occurs in the germinal centers of secondary lymphoid organs. This system is particularly relevant for indications in which B cell activation and antibody production have been implicated including, but not limited to, systemic lupus erythematosus (SLE), other autoimmune indications, hematological oncology and allergy.
Figure 1:
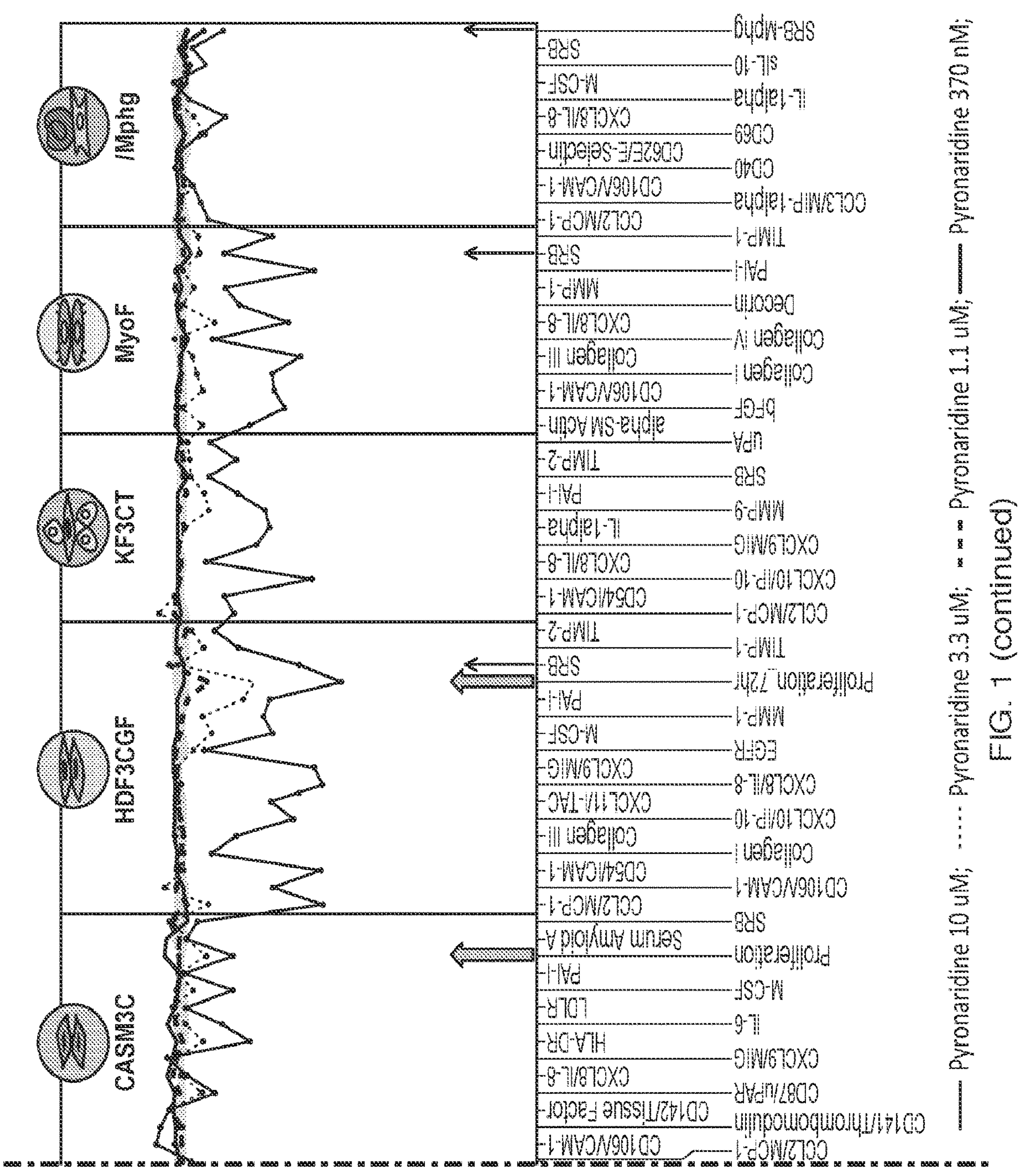
Figure 2:
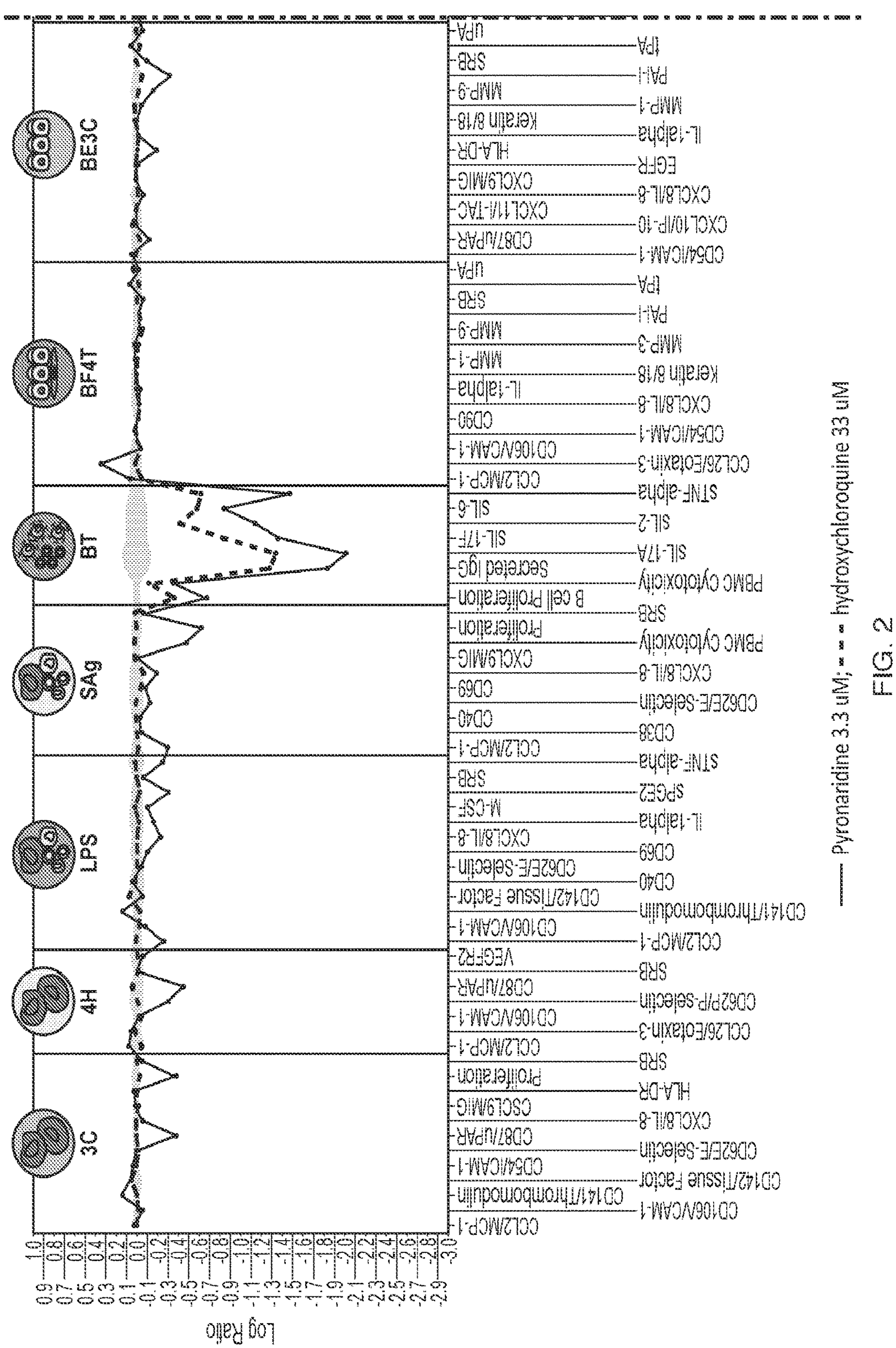
FIG. 2 shows an overlay of Pyronaridine at 3.3 μM and hydroxychloroquine at 33 μM in the BioMAP® Diversity PLUS panel at 10, 3.3, 1.1, and 0.3 μM. Hydroxychloroquine shows a noticeable similar pattern at a 10-fold decrease of concentration for Pyronaridine (i.e. 3.3 μM).
Figure 2:
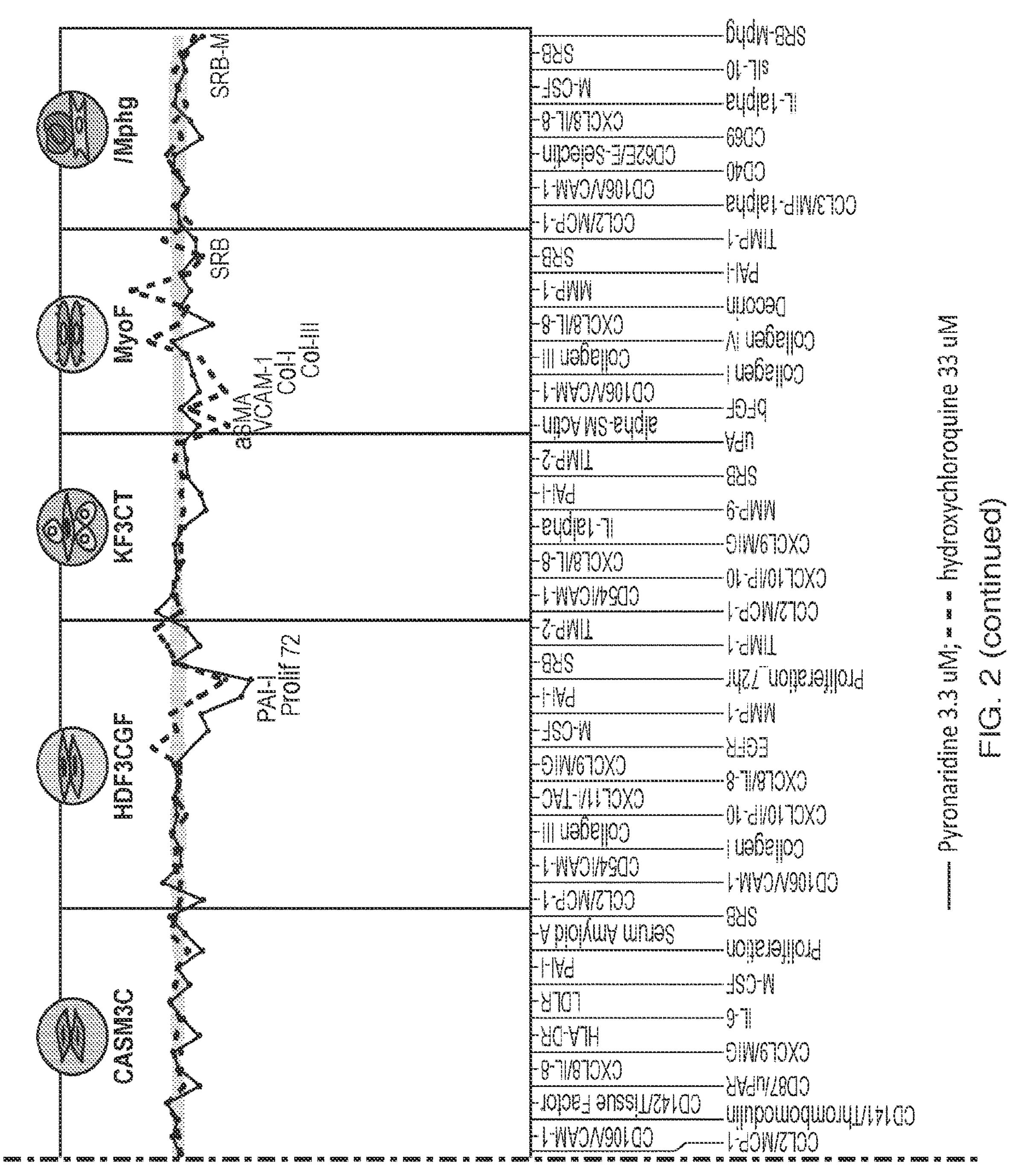

1. General Description of Compounds of the Invention

In certain aspects, the present invention provides for antagonists of TLR7/8. In some embodiments, such compounds include those of the formulae described herein, or a pharmaceutically acceptable salt thereof, wherein each variable is as defined and described herein.

2. Compounds and Definitions

Compounds of this invention include those described generally above, as well as pharmaceutically acceptable salts thereof, and/or mixtures thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. In some embodiments, the group comprises one or more deuterium atoms. There is furthermore intended that a compound of the invention includes isotope-labeled forms thereof. Examples of isotopes which are readily commercially available and which can be incorporated into a compound of the invention by well-known methods include isotopes of hydrogen, carbon, nitrogen, oxygen, phos-phorus, fluo-rine and chlorine, for example $^2H$, $^3H$, $^{13}C$, $^{14}C$, $^{15}N$, $^{18}O$, $^{17}O$, $^{31}P$, $^{32}P$, $^{35}S$, $^8F$ and $^{36}CI$, respectively. A compound of the invention, or a pharmaceutically acceptable salt thereof, either which contains one or more of the above-mentioned isotopes and/or other isotopes of other atoms is intended to be part of the present invention.

As used herein, the term "modulator" is defined as a compound that binds to and/or inhibits the target with measurable affinity. In certain embodiments, a modulator has an $IC_{50}$ and/or binding constant of less about 50 μM, less than about 1 μM, less than about 500 nM, less than about 100 nM, or less than about 10 nM.

The terms "measurable affinity" and "measurably inhibit," as used herein, means a measurable change in TLR7/8 activity between a sample comprising a compound of the present invention, or composition thereof, and TLR7/8, and an equivalent sample comprising TLR7/8, in the absence of said compound, or composition thereof.

3. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit TLR7/8 in a biological sample or in a patient. In certain embodiments, the amount of compound in compositions of this invention is such that is effective to measurably inhibit TLR7/8 in a biological sample or in a patient. In certain embodiments, a composition of this invention is formulated for administration to a patient in need of such composition.

The term "patient" or "subject", as used herein, means an animal, preferably a mammal, and most preferably a human.

The term "pharmaceutically acceptable carrier, adjuvant, or vehicle" refers to a nontoxic carrier, adjuvant, or vehicle that does not destroy the pharmacological activity of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention are administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

4. Uses of Compounds and Pharmaceutically Acceptable Compositions

The present invention furthermore relates to a method for treating a subject suffering from a TLR7/8 related disorder, comprising administering to said subject an effective amount of a compound of the invention selected from the group consisting of:

(I)

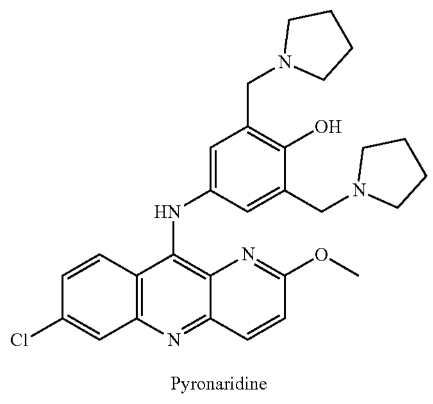

Pyronaridine

-continued (II)

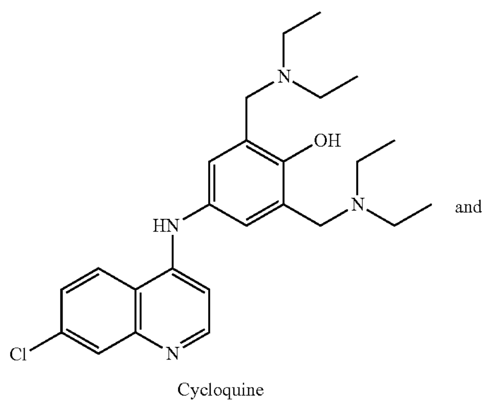

and

Cycloquine (III)

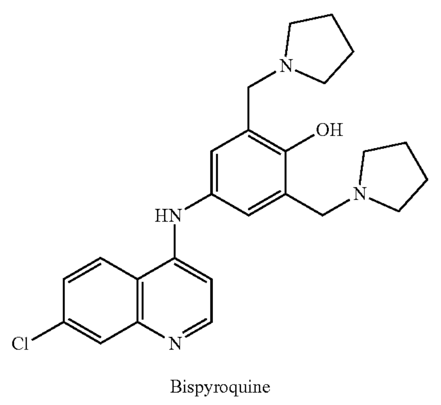

Bispyroquine and/or a pharmaceutically acceptable salt thereof.

The compounds of the present invention are useful as anticancer agents for cancers that are responsive to TLR7 activation. In certain embodiments, the cancers include, but are not limited to cancer of the breast, bladder, bone, brain, central and peripheral nervous system, colon, endocrine glands, esophagus, endometrium, germ cells, head and neck, kidney, liver, lung, larynx and hypopharynx, mesothelioma, sarcoma, ovary, pancreas, prostate, rectum, renal, small intestine, soft tissue, testis, stomach, skin, ureter, vagina and vulva; inherited cancers, retinomblastoma and Wilms tumor; leukemia, lymphoma, non-Hodgkins disease, chronic and acute myeloid leukaemia, acute lymphoblastic leukemia, Hodgkins disease, multiple myeloma and T-cell lymphoma; myelodysplastic syndrome, plasma cell neoplasia, paraneoplastic syndromes, cancers of unknown primary site and AIDS related malignancies.

In certain embodiments, the compounds of the invention are used to treat cancers of the skin or kidney. Sensitivity of a given cancer to activation of TLR7 can be assessed by, but not limited to measurement of a decrease in primary or metastatic tumor load (minor, partial or complete regression), alterations in the hemogram, altered hormone or cytokine concentrations in the blood, inhibition of further increase of tumor load, stabilization of the disease in the patient, assessment of biomarkers or surrogate markers relevant for the disease, prolonged overall survival of a patient, prolonged time to disease progression of a patient, prolonged progression-free survival of a patient, prolonged disease-free survival of a patient, improved quality of life of a patient, or modulation of the co-morbidity of the disease (for example, but not limited to pain, cachexia, mobilization, hopitalization, altered hemogram, weight loss, wound healing, fever).

The compounds according to the present invention may further be useful as immune response modifiers that can modulate the immune response in a number of different ways, rendering them useful in the treatment of a variety of disorders.

Provided herein are methods of inhibiting an immune response in an individual comprising administering to the individual an effective amount of an inhibitor of TLR7 and/or TLR8 (e.g., TLR inhibitor), using the compounds as described herein. In some variations, the TLR inhibitor inhibits a TLR7-dependent immune response. In some variations, the TLR inhibitor inhibits a TLR8-dependent immune response. In some variations, the TLR inhibitor inhibits a TLR7-dependent and a TLR8-dependent immune response. In some variations, the TLR inhibitor inhibits a TLR7-dependent, a TLR8-dependent, and another TLR-dependent immune response. Unless otherwise noted, the term TLR inhibitor refers to any one of the TLR inhibitors disclosed herein. In some preferred embodiments, the individual is a human patient.

Methods of immunoregulation are provided by the present disclosure and include those that suppress and/or inhibit an immune response, including, but not limited to, an immune response. The present disclosure also provides methods for ameliorating symptoms associated with unwanted immune activation, including, but not limited to, symptoms associated with autoimmunity. Immune suppression and/or inhibition according to the methods described herein may be practiced on individuals including those suffering from a disorder associated with an unwanted activation of an immune response. The present disclosure also provides methods for inhibiting a TLR7 and/or TLR8 induced response (e.g., in vitro or in vivo). In some variations, the cell is contacted with the TLR inhibitor in an amount effective to inhibit a response from the cell that contributes to an immune response.

Inhibition of TLR7 and/or TLR8 are useful for treating a variety of diseases or disorders that are responsive to cytokines. Conditions for which TLR7 and/or TLR8 inhibitors may be used as treatments include, but are not limited to, autoimmune diseases and inflammatory disorders. Provided herein are methods of treating a disease or disorder in an individual comprising administering to the individual an effective amount of an inhibitor of TLR7 and/or TLR8. Further, provided are methods for ameliorating symptoms associated with a disease or disorder comprising administering an effective amount of an inhibitor of TLR7 and/or TLR8 to an individual having the disease or disorder. Methods are also provided herein for delaying development of a disease or a disorder, comprising administering an effective amount of an inhibitor of one or more of TLR7 and/or TLR8 to an individual having the disease or the disorder. In certain embodiments, the inhibitor is a compound as described herein.

Provided herein are methods of inhibiting an immune response in an individual, the method comprising administering to the individual at least one TLR inhibitor as disclosed herein in an amount effective to inhibit the immune response in the individual. In some variations, the immune response is associated with an autoimmune disease. In further aspects, wherein inhibiting the immune response ameliorates one or more symptoms of the autoimmune disease. In still further aspects, wherein inhibiting the immune response treats the autoimmune disease. In yet further aspects, wherein inhibiting the immune response prevents or delays development of the autoimmune disease. In some variations, the TLR inhibitor inhibits a TLR7- dependent immune response. In some variations, the TLR inhibitor inhibits a TLR8-dependent immune response. In some variations, the TLR inhibitor inhibits a TLR7-dependent and a TLR8-dependent immune response. In some aspects, at least one TLR inhibitor is administered in an amount effective to inhibit an immune response in the individual.

Provided herein are also methods of treating or preventing an autoimmune disease in an individual, comprising administering to the individual an effective amount of a TLR7 and/or TLR8 inhibitor. In some aspects, the autoimmune disease is characterized by joint pain, antinuclear antibody positivity, malar rash, or discoid rash. In some aspects, the autoimmune disease is associated with the skin, muscle tissue, and/or connective tissue. In some embodiments, the autoimmune disease is not evidenced in the individual by skin, muscle tissue, and/or connective tissue symptoms. In some embodiments, the autoimmune disease is systemic. Autoimmune diseases include, without limitation, rheumatoid arthritis (RA), autoimmune pancreatitis (AIP), systemic lupus erythematosus (SLE), type I diabetes mellitus, multiple sclerosis (MS), antiphospholipid syndrome (APS), sclerosing cholangitis, systemic onset arthritis, irritable bowel disease (IBD), scleroderma, Sjogren's disease, vitiligo, polymyositis, pemphigus vulgaris, pemphigus *foliaceus*, inflammatory bowel disease including Crohn's disease and ulcerative colitis, autoimmune hepatitis, hypopituitarism, graft-versus-host disease (GvHD), autoimmune skin diseases, uveitis, pernicious anemia, and hypoparathyroidism. Autoimmune diseases may also include, without limitation, polyangiitis overlap syndrome, Kawasaki's disease, sarcoidosis, glomerulonephritis, and cryopathies.

In some aspects, the autoimmune disease is selected from the group consisting of arthritis, pancreatitis, mixed connective tissue disease (MCTD), lupus, antiphospholipid syndrome (APS), systemic onset arthritis, and irritable bowel syndrome.

In other aspects, the autoimmune disease is selected from the group consisting of systemic lupus erythematosus (SLE), rheumatoid arthritis, autoimmune skin disease, and multiple sclerosis.

In other aspects, the autoimmune disease is selected from the group consisting of pancreatitis, glomerulonephritis, pyelitis, sclerosing cholangitis, and type I diabetes. In some aspects, the autoimmune disease is rheumatoid arthritis. In some aspects, the autoimmune disease is autoimmune pancreatitis (AIP). In some aspects, the autoimmune disease is glomerulonephritis. In some aspects, the autoimmune disease is pyelitis. In some aspects, the autoimmune disease is sclerosing cholangitis. In some aspects the autoimmune disorder is psoriasis. In some aspects, the autoimmune disease is a rheumatoid disease or disorder. In some aspects, the rheumatoid disease or disorder is rheumatoid arthritis. In some aspects, the disease is diabetes and/or diabetic-related disease or disorder. In some aspects, wherein the autoimmune disease is associated with RNA-containing immune complexes. In some aspects, the autoimmune disease is Sjogren's disease.

Provided herein are methods of inhibiting an immune response in an individual, the method comprising administering to the individual at least one TLR inhibitor as disclosed herein in an amount effective to inhibit the immune response in the individual. In some variations, the immune response is associated with an inflammatory disorder. As used herein, the term "inflammatory disorder" encompasses autoimmune diseases, as well as inflammatory conditions without a known autoimmune component (e.g., atherosclerosis, asthma, etc.). In further aspects, inhibiting the immune response ameliorates one or more symptoms of the inflammatory disorder. In still further aspects, inhibiting the immune response treats the inflammatory disorder. In yet further aspects, inhibiting the immune response prevents or delays development of the inflammatory disorder. In some aspects, the inflammatory disorder is selected from the group consisting of non-rheumatoid arthritis, kidney fibrosis, and liver fibrosis. In some aspects, the inflammatory disorder is an interface dermatitis. In some further aspects, the interface dermatitis is selected from the group consisting of lichen planus, lichenoid eruption, lichen planus-like keratosis, lichen *striatus*, keratosis lichenoides chronica, erythema multiforme, fixed drug eruption, *pityriasis* lichenoides, phototoxic dermatitis, radiation dermatitis, viral exanthems, dermatomyositis, secondary syphilis, lichen sclerosus et atrophicus, mycosis fungoides, bullous pemphigoid, lichen *aureus*, porokeratosis, acrodermatitis chronicus atrophicans, and regressing melanoma. In some aspects, the inflammatory condition is a skin disorder such as atopic dermatitis (eczema). In some aspects, the inflammatory disorder is a sterile inflammatory condition such as drug-induced liver and/or pancreas inflammation. In some further aspects, the inflammatory disease is an inflammatory liver disorder. In some other further aspects, the inflammatory disease is an inflammatory pancreatic disorder.

Provided herein are methods of inhibiting an immune response in an individual, the method comprising administering to the individual at least one TLR inhibitor as disclosed herein in an amount effective to inhibit the immune response in the individual. In some variations, the immune response is associated with chronic pathogen stimulation. In some variations, the immune response is associated with infection by HIV. In further aspects, wherein inhibiting the immune response ameliorates one or more symptoms of the viral disease or disorder resulting from infection by HIV. In still further aspects, wherein inhibiting the immune response treats the viral disease or disorder resulting from infection by HIV. In yet further aspects, wherein inhibiting the immune response prevents or delays development of the viral disease or disorder resulting from infection by HIV. Other variations provided herein relate to immunoinhibitory therapy of individuals having been exposed to or infected with HIV. Administration of a TLR inhibitor to an individual having been exposed to or infected with HIV results in suppression of HIV induced cytokine production. In some aspects, at least one TLR inhibitor is administered in an amount effective to suppress HIV induced cytokine production in an individual exposed to or infected with a HIV.

Provided herein are methods for inhibiting a TLR7 and/or TLR8-dependent immune response in an individual, the method comprising administering to the individual a TLR inhibitor in an amount effective to inhibit the immune response in the individual. In some variations, the immune response is associated with an autoimmune disease. In some aspects, the autoimmune disease is rheumatoid arthritis. In some aspects, the TLR inhibitor is effective in suppressing one or more symptoms of rheumatoid arthritis. In some aspects, the autoimmune disease is multiple sclerosis. In some aspects, the TLR inhibitor is effective in suppressing one or more symptoms of multiple sclerosis. In some aspects, the autoimmune disease is lupus. In some aspects, the TLR inhibitor is effective in suppressing one or more symptoms of lupus. In some aspects, the autoimmune disease is pancreatitis. In some aspects, the TLR inhibitor is effective in suppressing one or more symptoms of pancreatitis. In some aspects, the autoimmune disease is diabetes. In some aspects, the TLR inhibitor is effective in suppressing one or more symptoms of diabetes. In some aspects, the disease is Sjogren's disease. In some aspects, the TLR inhibitor is effective in suppressing one or more symptoms of Sjogren's disease. In some variations, the immune response is associated with an inflammatory disorder. In some aspects, the TLR inhibitor is effective in suppressing one or more symptoms of an inflammatory disorder. In some variations, the immune response is associated with chronic pathogen stimulation. In some aspects, the TLR inhibitor is effective in suppressing one or more symptoms of chronic pathogen stimulation. In some variations, the immune response is associated with viral disease resulting from infection with HIV. In some aspects, the TLR inhibitor is effective in suppressing one or more symptoms of viral disease resulting from infection with HIV.

In some embodiments of any of the methods involving administration of a TLR inhibitor to an individual (e.g., methods of inhibiting an immune response, or treating an autoimmune disease or inflammatory disorder, etc.) the TLR inhibitor has a therapeutically acceptable safety profile. The TLR inhibitor may for example, have a therapeutically acceptable histological profile including an acceptably low, if any, toxicity of the liver, kidney, pancreas, or other organs. In some embodiments, the TLR inhibitor has a safety profile that is unexpected and advantageous. In some embodiments, a safety profile includes evaluation of toxicity, histological profile, and/or necrosis (e.g., liver, kidneys and/or heart). In some embodiments, the TLR inhibitor has a therapeutically acceptable level of toxicity. In some embodiments, the TLR inhibitor has a reduced level of toxicity as compared to another TLR inhibitor. In some embodiments, the TLR inhibitor induces a therapeutically acceptable reduction in body weight as compared to the initial body weight of a treated individual. In some embodiments, the TLR inhibitor induces less than 5%, 7.5%, 10%, 12.5, or 15% reduction in total body weight. In some embodiments, the TLR inhibitor has a therapeutically acceptable histology profile. In some embodiments, the TLR inhibitor has a better (e.g., lower severity score) histology profile, for example, as compared to a reference TLR inhibitor. In some embodiments, the TLR inhibitor has a better (e.g., lower severity score) histology profile upon evaluation of the liver, kidneys and/or heart, for example. In some embodiments, the TLR inhibitor has a therapeutically acceptable necrosis score. In some embodiments, the TLR inhibitor has reduced necrosis and/or better (e.g., lower) necrosis score, for example, as compared to a reference TLR inhibitor. In some embodiments, the TLR inhibitor has reduced renal and/or hepatocellular necrosis and/or a better renal and/or hepatocellular necrosis score, for example, as compared to a reference TLR inhibitor.

Accordingly, the invention provides a method of activating TLR7 in an animal, especially a mammal, preferably a human comprising administering an effective amount of a compound of the invention, or a pharmaceutically acceptable salt thereof, to the animal. As with all compositions for inhibition of an immune response, the effective amounts and method of administration of the particular TLR inhibitor formulation can vary based on the individual, what condition is to be treated and other factors evident to one skilled in the art. An effective amount of a compound will vary according to factors known in the art but is expected to be a dose of about 0.1 to 10 mg/kg, 0.5 to 10 mg/kg, 1 to 10 mg/kg, 0.1 to 20 mg/kg, 0.1 to 20 mg/kg, or 1 to 20 mg/kg.

The invention also provides a method of treating a viral infection in an animal comprising administering an effective amount of a compound of Formula I to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount will vary according to factors known in the art but is expected to be a dose as indicated above with respect to the activation of TLR7, or a dose of about 100 ng/kg to about 50 mg/kg, preferably about 10 μg/kg to about 5 mg/kg. In one aspect of this embodiment, the viral infection is caused by a coronavirus. In a further aspect of this embodiment, the coronavirus is selected from SARS (Severe Acute Respiratory Syndrome), MERS (Middle East Respiratory Syndrome), and COVID-19. In one aspect of this embodiment, the viral infection is from COVID-19.

The method of the invention can be performed either in vitro or in vivo. The susceptibility of a particular cell to treatment with the compounds according to the invention can be particularly determined by in vitro tests, whether in the course of research or clinical application. Typically, a culture of the cell is combined with a compound according to the invention at various concentrations for a period of time which is sufficient to allow the active agents to inhibit TLR7/8 activity, usually between about one hour and one week. In vitro treatment can be carried out using cultivated cells from a biopsy sample or cell line.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing TLR7/8-dependent signal transduction pathways in animals and/or cell culture models or in the clinical diseases mentioned in this application.

Moreover, the subsequent teaching of the present specification concerning the use of the compounds according to the invention for the production of a medicament for the prophylactic or therapeutic treatment and/or monitoring is considered as valid and applicable without restrictions to the use of the compound for the inhibition of TLR7/8 activity if expedient.

The invention also relates to the use of compounds according to the invention, or a pharmaceutically acceptable salt thereof, for the therapeutic treatment and/or monitoring of diseases that are caused, mediated and/or propagated by TLR7/8 activity. Furthermore, the invention relates to the use of compounds according to the invention, or a pharmaceutically acceptable salt thereof, for the production of a medicament for the prophylactic or therapeutic treatment and/or monitoring of diseases that are caused, mediated and/or propagated by TLR7/8 activity. In certain embodiments, the invention provides the use of a compound according to invention, or a pharmaceutically acceptable salt thereof, for the production of a medicament for the prophylactic or therapeutic treatment of a TLR7/8-mediated disorder.

The compounds according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to boost the response and eradicate the pathogens and/or symptoms of the disease completely. Either the identical compound or different compounds can be applied. The methods of the invention can also be used to reduce the likelihood of developing a disorder or even prevent the initiation of disorders associated with TLR7/8 activity in advance or to treat the arising and continuing symptoms.

The invention furthermore relates to a medicament comprising at least one compound according to the invention and/or pharmaceutically acceptable salts thereof, including mixtures thereof in all ratios. In certain embodiments, the invention relates to a medicament comprising at least one compound according to the invention and/or a pharmaceutically acceptable salt thereof.

A “medicament” in the meaning of the invention is any agent in the field of medicine, which comprises one or more compounds of the invention or preparations thereof (e.g. a pharmaceutical composition or pharmaceutical formulation) and can be used in therapy, follow-up or aftercare of patients who suffer from diseases, which are associated with TLR7/8 activity, in such a way that a pathogenic modification of their overall condition or of the condition of particular regions of the organism could establish at least temporarily.

In various embodiments, the active ingredient may be administered alone or in combination with other treatments. A synergistic effect may be achieved by using more than one compound in the pharmaceutical composition, i.e. the compound of the invention is combined with one or more additional active ingredients, which is either another compound of the invention or a compound of different structural scaffold. The active ingredients can be used either simultaneously or sequentially.

In some embodiments, a TLR inhibitor as described herein is administered in combination with a corticosteroid. In some embodiments, the corticosteroid is a glucocorticosteroid. In some embodiments, the corticosteroid is a mineralocorticoid. Corticosteroids include, but are not limited to, corticosterone and derivatives, prodrugs, isomers and analogs thereof, cortisone and derivatives, prodrugs, isomers and analogs thereof (i.e., Cortone), aldosterone and derivatives, prodrugs, isomers and analogs thereof, dexamethasone and derivatives, prodrugs, isomers and analogs thereof (i.e., Decadron), prednisone and derivatives, prodrugs, isomers and analogs thereof (i.e., Prelone), fludrocortisones and derivatives, prodrugs, isomers and analogs thereof, hydrocortisone and derivatives, prodrugs, isomers and analogs thereof (i.e., cortisol or Cortef), hydroxycortisone and derivatives, prodrugs, isomers and analogs thereof, betamethasone and derivatives, prodrugs, isomers and analogs thereof (i.e., Celestone), budesonide and derivatives, prodrugs, isomers and analogs thereof (i.e., Entocort EC), methylprednisolone and derivatives, prodrugs, isomers and analogs thereof (i.e., Medrol), prednisolone and derivatives, prodrugs, isomers and analogs thereof (i.e., Deltasone, Crtan, Meticorten, Orasone, or Sterapred), triamcinolone and derivatives, prodrugs, isomers and analogs thereof (i.e., Kenacort or Kenalog), and the like. In some embodiments, the corticosteroid is fludrocortisone or a derivative, prodrug, isomer or analog thereof. In some embodiments, the corticosteroid is fludrocortisone. In some embodiments, the corticosteroid is hydroxycortisone or a derivative, prodrug, isomer or analog thereof. In some embodiments, the corticosteroid is hydroxycortisone.

In some embodiments, the corticosteroid is administered between about any of 0.001 mg to 1 mg, 0.5 mg to 1 mg, 1 mg to 2 mg, 2 mg to 20 mg, 20 mg to 40 mg, 40 to 80 mg, 80 to 120 mg, 120 mg to 200 mg, 200 mg to 500 mg, or 500 mg to 1000 mg per day. In some embodiments, the corticosteroid is administered between about any of 0.1 mg/kg to 0.5 mg/kg, 0.5 mg/kg to 1 mg/kg, 1 mg/kg to 2 mg/kg, 2 mg/kg to 5 mg/kg, 5 mg/kg to 10 mg/kg, 10 mg/kg to 15 mg/kg, 15 mg/kg to 20 mg/kg, 20 mg/kg to 25 mg/kg, 25 mg/kg to 35 mg/kg, or 35 mg/kg to 50 mg/kg per day.

In some embodiments, the TLR inhibitor used in combination therapy, given in amounts of the TLR inhibitor delivered, may be, for example, from about any of 0.1 to 10 mg/kg, 0.5 to 10 mg/kg, 1 to 10 mg/kg, 0.1 to 20 mg/kg, 0.1 to 20 mg/kg, or 1 to 20 mg/kg.

In some embodiments, the TLR inhibitor is administered simultaneously with one or more additional active ingredients including, but not limited to, a corticosteroid (simultaneous administration). In some embodiments, the TLR inhibitor is administered sequentially with an additional therapeutic agent including, but not limited to, a corticosteroid (sequential administration). In some embodiments, sequential administration includes administering the TLR inhibitor or additional therapeutic agent followed within about any of one minutes, five minutes, 30 minutes, one hour, five hours, 24 hours, 48 hours, or a week. In some embodiments, the TLR inhibitor is administered by the same route of administration as the additional therapeutic agent. In some embodiments, the TLR inhibitor is administered by a different route of administration than the additional therapeutic agent. In some embodiments, the additional therapeutic agent is administered parentally (e.g., central venous line, intra-arterial, intravenous, intramuscular, intraperitoneal, intradermal, or subcutaneous injection), orally, gastrointestinally, topically, naso-pharyngeal and pulmonary (e.g. inhalation or intranasally). In some embodiments, the additional therapeutic agent is a corticosteroid.

The disclosed compounds of the invention can be administered in combination with one or more additional active ingredients, including anticancer agents. As used here, the term “anticancer agent” relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating agents: such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-3024, VAL-0834;

Platinum Compounds: such as carboplatin, cisplatin, eptaplatin, miriplatine hydrate, oxaliplatin, lobaplatin, nedaplatin, picoplatin, satraplatin; lobaplatin, nedaplatin, picoplatin, satraplatin;

DNA altering agents: such as amrubicin, bisantrene, decitabine, mitoxantrone, procarbazine, trabectedin, clofarabine; amsacrine, brostallicin, pixantrone, laromustine[1,3];

Topoisomerase Inhibitors: such as etoposide, irinotecan, razoxane, sobuzoxane, teniposide, topotecan; amonafide, belotecan, elliptinium acetate, voreloxin;

Microtubule modifiers: such as cabazitaxel, docetaxel, eribulin, ixabepilone, paclitaxel, vinblastine, vincristine, vinorelbine, vindesine, vinflunine; fosbretabulin, tesetaxel;

Antimetabolites: such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2,3], trimetrexate;

Anticancer antibiotics: such as bleomycin, dactinomycin, doxorubicin, epirubicin, idarubicin, levamisole, miltefosine, mitomycin C, romidepsin, streptozocin, valrubicin, zinostatin, zorubicin, daunurobicin, plicamycin; aclarubicin, peplomycin, pirarubicin;

Hormones/Antagonists: such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[1,3];

Aromatase inhibitors: such as aminoglutethimide, anastrozole, exemestane, fadrozole, letrozole, testolactone; formestane;

Small molecule kinase inhibitors: such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];

Photosensitizers: such as methoxsalen[3]; porfimer sodium, talaporfin, temoporfin;

Antibodies: such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3] EMD-525797[4], nivolumab[1,3];

Cytokines: such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates: such as denileukin diftitox, ibritumomab tiuxetan, iobenguane I123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab[1,3], vintafolide[1,3];

Vaccines: such as sipuleucel[3]; vitespen[3], emepepimut-S[3], oncoVAX[4], rindopepimut[3], troVax[4], MGN-1601[4], MGN-1703[4]; and Miscellaneous: alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3] endostatin[4], immucothel[4], belinostat[3], MGN-1703[4].

([1]Prop. INN (Proposed International Nonproprietary Name); [2]Rec. INN (Recommended International Nonproprietary Names); [3] USAN (United States Adopted Name); [4] no INN).

In some embodiments, the combination of a TLR inhibitor with one or more additional active ingredients reduces the effective amount (including, but not limited to, dosage volume, dosage concentration, and/or total drug dose administered) of the TLR inhibitor and/or the one or more additional active ingredients administered to achieve the same result as compared to the effective amount administered when the TLR inhibitor or the additional active ingredient is administered alone. In some embodiments, the combination of a TLR inhibitor with a corticosteroid reduces the effective amount of corticosteroid administered as compared to the corticosteroid administered alone. In some embodiments, the combination of a TLR inhibitor with the one or more additional active ingredients reduces the frequency of administrations of the therapeutic agent compared to administration of the additional active ingredient(s) alone. In some embodiments, the combination of a TLR inhibitor with the one or more additional active ingredient reduces the total duration of treatment compared to administration of the additional active ingredient alone. In some embodiments, the combination of a TLR inhibitor with the one or more additional active ingredient reduces the side effects associated with administration of the additional active ingredient alone. In some embodiments, the one or more additional active ingredient is a corticosteroid. In some embodiments, the corticosteroid is fludrocortisone or a derivative, prodrug, isomer or analog thereof. In some embodiments, the corticosteroid is fludrocortisone. In some embodiments, the combination of an effective amount of the TLR inhibitor with the additional active ingredient is more efficacious compared to an effective amount of the TLR inhibitor or the additional active ingredient alone.

In some embodiments, a TLR inhibitor as described herein is administered in combination with an antiviral agent. In one aspect of this embodiment, the antiviral agent is remdesivir. In one aspect of this embodiment, the combination is useful to treat a viral infection. In a further aspect of this embodiment, the viral infection is caused by a coronavirus. In one aspect of this, the coronavirus is COVID-19.

TLR inhibitors also may be useful as a vaccine adjuvant for use in conjunction with any material that modulates either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; recombinant proteins; glycoproteins; peptides; and the like. In some aspects, the combination therapy including but not limited to the combination of a TLR inhibitor and a vaccine is used in the treatment of an autoimmune disease or an inflammatory disorder. In some aspects, the combination therapy including but not limited to the combination of a TLR inhibitor and a vaccine is used in the treatment of an infectious disease.

In some embodiments, the combination therapy including but not limited to the combination of a TLR inhibitor and a corticosteroid is used in the treatment of an autoimmune disease or an inflammatory disorder. In some embodiments, the autoimmune disease is selected from but not limited to rheumatoid arthritis, systemic lupus erythematosus, autoimmune skin disease, multiple sclerosis, pancreatitis, glomerulonephritis, pyelitis, Sclerosing cholangitis, and type I diabetes. In some embodiments, the autoimmune disease is Sjogren's disease.

Also provided herein are kits comprising a TLR inhibitor as provided herein, and instructions for use in the methods of inhibiting a TLR7- and/or TLR8-dependent immune response.

The kits may comprise one or more containers comprising a TLR inhibitor (or a formulation comprising a TLR inhibitor) as described herein, and a set of instructions, generally written instructions although electronic storage media (e.g., magnetic diskette or optical disk) containing instructions are also acceptable, relating to the use and dosage of the TLR inhibitor or formulation for the intended treatment (e.g., suppression of a response to a TLR7 and/or TLR8 agonists, suppression of a TLR7 and/or TLR8-dependent immune response, ameliorating one or more symptoms of an autoimmune disease, ameliorating a symptom of chronic inflammatory disease, decreasing cytokine production in response to a virus, and/or treating one or more symptoms of a disease or disorder mediated by TLR7 and/or TLR8). The instructions included with the kit generally include information as to dosage, dosing schedule, and route of administration for the intended treatment. The containers for the TLR inhibitor (or formulations comprising a TLR inhibitor) may be unit doses, bulk packages (e.g., multi-dose packages) or sub-unit doses. The kits may further comprise a container comprising an adjuvant.

In another aspect, the invention provides for a kit consisting of separate packs of an effective amount of a compound according to the invention and/or a pharmaceutically acceptable salt thereof, including mixtures thereof in all ratios, and optionally, an effective amount of one or more additional active ingredients. The kit comprises suitable containers, such as boxes, individual bottles, bags or ampoules. The kit may, for example, comprise separate ampoules, each containing an effective amount of a compound according to the invention and/or a pharmaceutically acceptable salt thereof, and an effective amount of one or more additional active ingredients in dissolved or lyophilized form.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms, exposure to a known disease vector, and/or in light of genetic or other susceptibility factors). Treatment may also include administration after some or all symptoms have resolved, for example to prevent or delay their recurrence.

According to one embodiment, the invention relates to a method of inhibiting TLR7/8 activity in a biological sample comprising the step of contacting said biological sample with a compound of this invention, or a composition comprising said compound.

According to another embodiment, the invention relates to a method of inhibiting TLR7/8, or a mutant thereof, activity in a biological sample in a positive manner, comprising the step of contacting said biological sample with a compound of this invention, or a composition comprising said compound.

The compounds of the invention are useful in-vitro as unique tools for understanding the biological role of TLR7/8, including the evaluation of the many factors thought to influence, and be influenced by, the production of TLR7/8 and the interaction of TLR7/8. The present compounds are also useful in the development of other compounds that interact with TLR7/8 since the present compounds provide important structure-activity relationship (SAR) information that facilitate that development. Compounds of the present invention that bind to TLR7/8 can be used as reagents for detecting TLR7/8 in living cells, fixed cells, in biological fluids, in tissue homogenates, in purified, natural biological materials, etc. For example, by labeling such compounds, one can identify cells expressing TLR7/8. In addition, based on their ability to bind TLR7/8, compounds of the present invention can be used in in-situ staining, FACS (fluorescence-activated cell sorting), sodium dodecyl sulfate polyacrylamide gel electrophoresis (SDS-PAGE), ELISA (enzyme-linked immunoadsorptive assay), etc., enzyme purification, or in purifying cells expressing TLR7/8 inside permeabilized cells. The compounds of the invention can also be utilized as commercial research reagents for various medical research and diagnostic uses. Such uses can include but are not limited to: use as a calibration standard for quantifying the activities of candidate TLR7/8 inhibitors in a variety of functional assays; use as blocking reagents in random compound screening, i.e. in looking for new families of TLR7/8 ligands, the compounds can be used to block recovery of the presently disclosed TLR7/8 compounds; use in the co-crystallization with TLR7/8, i.e. the compounds of the present invention will allow formation of crystals of the compound bound to TLR7/8, enabling the determination of enzyme/compound structure by x-ray crystallography; other research and diagnostic applications, wherein TLR7/8 is preferably activated or such activation is conveniently calibrated against a known quantity of an TLR7/8 inhibitor, etc.; use in assays as probes for determining the expression of TLR7/8 in cells; and developing assays for detecting compounds which bind to the same site as the TLR7/8 binding ligands.

The compounds of the invention can be applied either themselves and/or in combination with physical measurements for diagnostics of treatment effectiveness. Pharmaceutical compositions containing said compounds and the use of said compounds to treat TLR7/8-mediated conditions is a promising, novel approach for a broad spectrum of therapies causing a direct and immediate improvement in the state of health, whether in human or in animal. The orally bioavailable chemical entities of the invention improve convenience for patients and compliance for physicians.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of TLR7/8, or a mutant thereof, activity in a biological sample is useful for a variety of purposes that are known to one of skill in the art. Examples of such purposes include, but are not limited to, blood transfusion, organ transplantation, biological specimen storage, and biological assays.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

The symbols and conventions used in the following descriptions of processes, schemes, and examples are consistent with those used in the contemporary scientific literature, for example, the Journal of the American Chemical Society or the Journal of Biological Chemistry.

Example 1: Synthesis of Compound 1

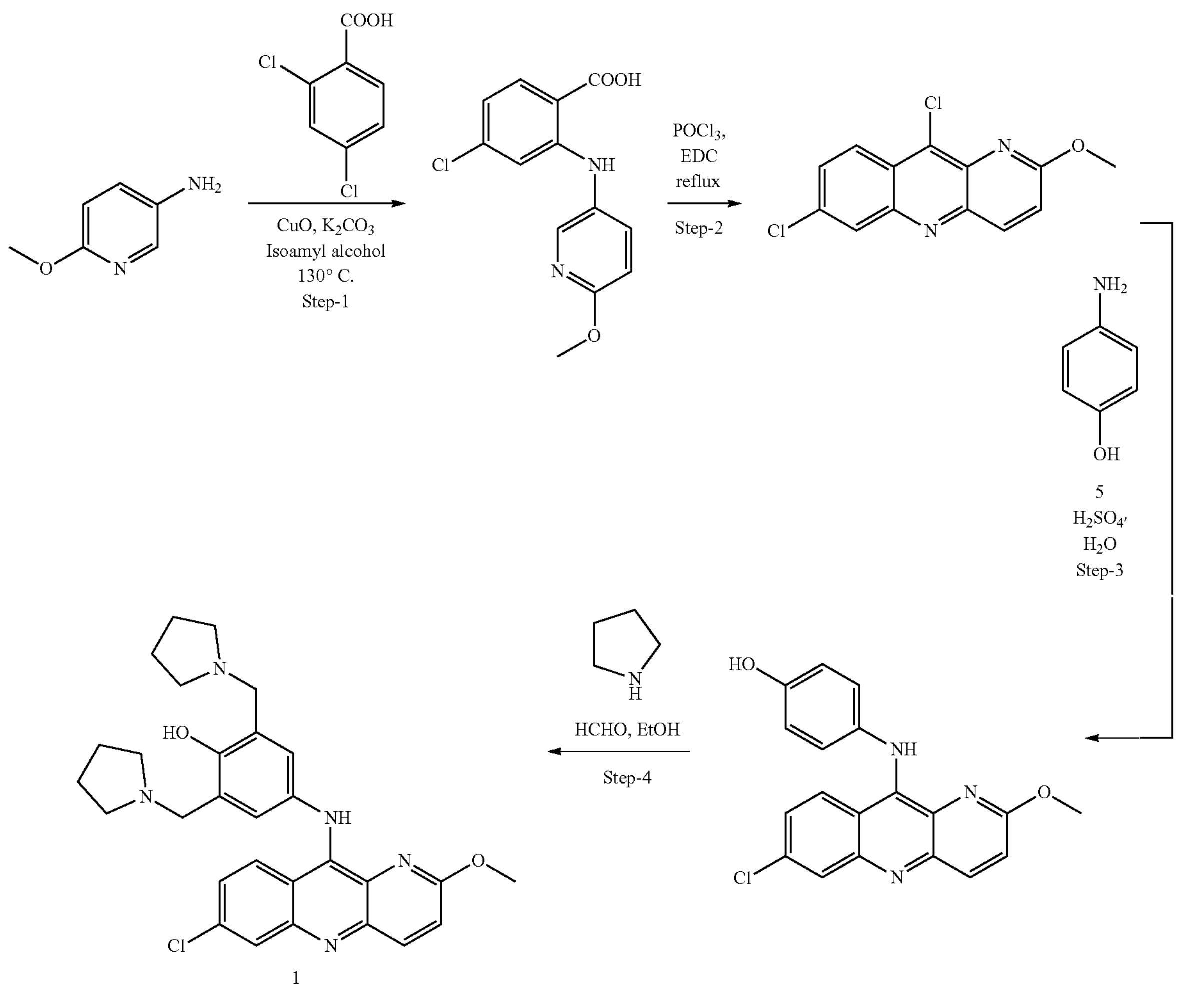

Step-1: The suspension of 2,4-dichlorobenzoic acid (35.7 g, 0.186 mol), 6-methoxypyridin-3-amine (25 g, 0.201 mol), potassium carbonate (13 g, 0.094 mol), and CuO (0.15 g, 0.38 mol) in 100 mL isopentanol was refluxed at 130° C., with the production of $CO_2$ gas. The reaction was cooled to 100° C. after 10 h and quenched with 35 mL water. Then, the pH of the solvent was adjusted to 11 with 10% $NaOHa_q$ at the same temperature. The obtained solution was cooled to 40-50° C. and filtered to remove the copper salt. The filtrate was adjusted to pH 3 with 6 N HCl to obtain a grey precipitate. The precipitate was slurried with hexane, filtered and dried to afford a 4-Chloro-2-(6-methoxy-pyridin-3-yl-amino)-benzoic acid (42 g, 94.09%). LCMS: Calculated for $C_{13}H_{11}ClN_2O_3$ 278.69, Observed 279.1 (M+H), RT. 2.27 min, 99.30% (Max). $^1$H NMR (400 MHz, DMSO-d$^6$): δ 9.48 (s, 1H), 8.13 (d, J=2.80 Hz, 1H), 7.88 (d, J=8.40 Hz, 1H), 7.70 (dd, J=2.80, 8.80 Hz, 1H), 6.90 (d, J=8.80 Hz, 1H), 6.75 (dd, J=2.00, 8.40 Hz, 1H), 6.68 (d, J=1.60 Hz, 1H), 3.87 (s, 3H).

Step-2: To a stirred solution of 4-chloro-2-(6-methoxy-pyridin-3-yl-amino)-benzoic acid (7 g, 0.025 mol) in ethylene dichloride (35 mL), was added $POCl_3$ (11.6 mL, 0.125 mol). The mixture was heated to reflux temperature for 2 h. The reaction mixture was cooled to 10° C. and MeOH (53 mL) was added carefully in the mixture followed by adding a solution of sodium hydroxide. The mixture was stirred for 2 h at 20-30° C. The crude product was filtered, washed with MeOH and water. Then dried under vacuum to get 7,10-dichloro-2-methoxybenzo[b]-1,5-naphthyridine (3.5 g, 49.92%). LCMS: Calculated for $C_{13}H_8Cl_2N_2O$ 279.12, Observed 281.0 (M+H), RT. 3.21 min, 97.58% (Max). $^1H$ NMR (400 MHz, DMSO-$d^6$): δ 8.46 (d, J=3.60 Hz, 1H), 8.43 (d, J=3.60 Hz, 1H), 8.31 (d, J=2.00 Hz, 1H), 7.85 (dd, J=2.00, 9.20 Hz, 1H), 7.52 (d, J=9.20 Hz, 1H), 4.16 (s, 3H).

Step-3: To a stirred solution of 4-aminophenol (6.7 g, 0.061 mol) in purified water (196 mL), sulfuric acid (12.0 g, 0.122 mol) was added followed by 7,10-dichloro-2-methoxybenzo[b]-1,5-naphthyridine (13.0 g, 0.047 mol). The mixture was heated to 85° C. for 7 h and refluxed for 10 h. The reaction mixture was cooled to 10-30° C. and a solution of sodium hydroxide is added to the reaction mixture. The mixture was stirred for 1 h at 10-30° C. Then filtered, washed with water and methanol to get 4-[(7-Chloro-2-methoxybenzo[b]-1,5-naphthyridin-10-yl)amino]-phenol hemisulphate (17.3 g, 82.97%). LCMS: Calculated for $C_{19}H_{14}ClN_3O_2$ 351.79, Observed 352.2 (M+H), RT. 1.54 min, 96.09% (Max). $^1H$ NMR (400 MHz, DMSO-$d^6$): δ 9.92 (s, 1H), 9.64 (s, 1H), 8.22 (d, J=9.16 Hz, 1H), 7.92 (d, J=1.48 Hz, 1H), 7.74 (d, J=8.96 Hz, 1H), 7.43 (d, J=9.20 Hz, 1H), 3.79 (d, J=2809.32 Hz, 1H), 7.15 (d, J=8.56 Hz, 2H), 6.84 (d, J=8.60 Hz, 2H), 3.94 (s, 3H).

Step-4: To a stirred solution of paraformaldehyde (29.3 g, 0.977 mol) in ethanol (110 mL), was added pyrrolidine (69.54 g, 0.977 mol) after cooling to −5° C. to 5° C. Then the reaction mixture was heated to 70° C. for 15 minutes. The mixture was cooled to 25-35° C. and 4-[(7-Chloro-2-methoxybenzo[b]-1,5-naphthyridin-10-yl)amino]-phenol hemisulphate (17.2 g, 0.0488 mol) was added to the mixture. The mixture was stirred for 15 h at 50° C. After the completion of the reaction, purified water (140 mL) was added and the mixture cooled to 15-25° C. The mixture was stirred for at 1 h, filtered and the product was washed with purified water (36.0 mL). Methanol (140 mL) was added and the mixture was heated at reflux for 1 h. The mixture was cooled to 5-15° C., stirred for at 2 h and filtered. Then washed with methanol (40 mL) and dried under vacuum to yield 1 (20.3 g, 79.70%). LCMS: Calculated for $C_{29}H_{32}ClN_5O_2$ 518.06, Observed 518.06 (M+H), RT. 1.41 min, 99.29% (Max), HPLC: RT: 2.58 min, 99.66% (Max).

$^1H$ NMR (400 MHz, DMSO-$d^6$): δ 9.05 (s, 1H), 8.21 (d, J=9.20 Hz, 1H), 7.93 (d, J=2.00 Hz, 1H), 7.77 (d, J=9.20 Hz, 1H), 7.31 (d, J=9.20 Hz, 1H), 7.18 (dd, J=2.00, 9.40 Hz, 1H), 3.94 (s, 3H), 3.65 (s, 4H), 2.50 (m, 8H), 1.69 (s, 8H). $^{13}C$ NMR (100 MHz, DMSO-d6): δ 159.2, 15216, 148.2, 144.3, 142.7, 10.1, 133.8, 133.5, 127.7, 127.5, 126.8, 124.1, 122.9, 122.8, 118.9, 115.0, 55.1, 53.7, 53.1, 23.1.

Example 2: Synthesis of Compound 2

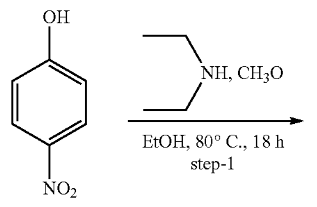

-continued

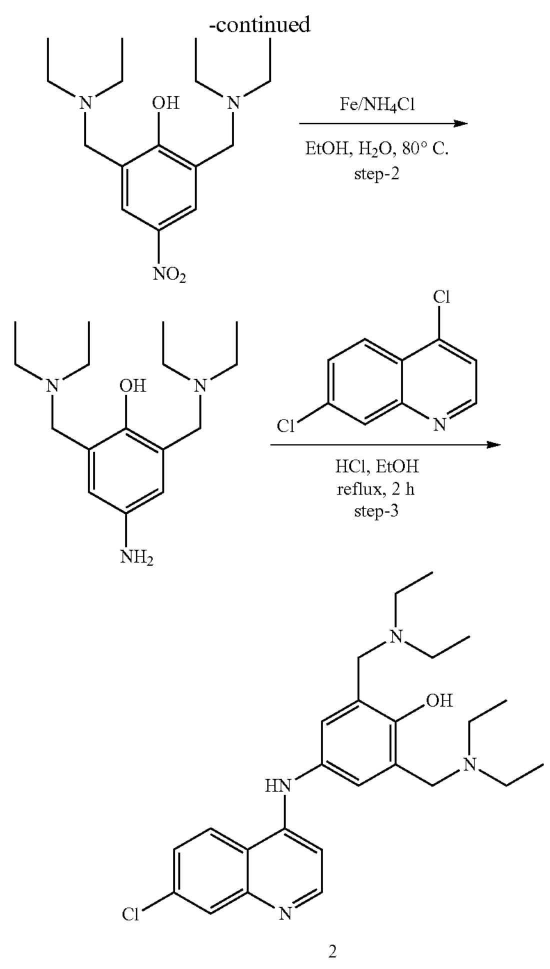

2

Step-1: 4-aminophenol (3 g, 21 mmol), diethylamine (9.8 mL, 94 mmol) and para formaldehyde (2.85 g, 94 mmol) were taken in 20 mL of ethanol in a sealed tube and stirred at 80° C. for 18 h. The reaction mixture was then evaporated, and the residue was purified by column chromatography to get 2,6-bis((diethylamino)methyl)-4-nitrophenol (1 g, 14.99%). LCMS: Calculated for $C_{16}H_{27}N_3O_3$ 309.41, Observed 310.2 (M+H), RT. 0.36 min, 82.7% (Max), $^1H$ NMR (400 MHz. DMSO-$d^6$): δ 8.00 (s, 2H), 3.77 (s, 4H), 2.63-2.68 (m, 8H), 1.06 (t, J=7.12 Hz, 12H).

Step-2: To a stirred suspension of 2,6-bis((diethylamino) methyl)-4-nitrophenol (1 g, 3.23 mmol) in ethanol, water (30 mL, 20:10) was added iron powder (1.4 g, 25.8 mmol) and $NH_4Cl$ (1.36 g, 25.8 mmol). The reaction mixture was heated to 80° C. for 2 h. The completion of the reaction was confirmed by TLC. The resulting reaction mixture was filtered through a bed of celite, washed with dichloromethane and concentrated to afford 4-amino-2,6-bis((diethyl amino)methyl)phenol (0.8 g) as a brown solid, proceed for the next step as such. LCMS: Calculated for $C_{16}H_{29}N_3O$ 279.43, Observed 280.2 (M+H), RT. 0.31 min, 89.3% (Max).

Step-3: To a stirred solution of 4-amino-2,6-bis((diethyl-amino)methyl)phenol (0.8 g, 2.86 mmol) and 4,7-dichloro-quinoline (0.68 g, 3.43 mmol) in 50 mL of ethanol, was added 0.5 mL conc. HCl and heated to reflux for overnight. The reaction mixture was then evaporated and the residue was purified by column chromatography to yield 2 (0.7 g, 57.3%) as reddish orange solid. LCMS: Calculated for $C_{25}H_{33}ClN_4O$ 441.02, Observed 441.2 (M+H), RT. 1.01 min, 97.61% (Max), HPLC: RT 1.97 min, 96.21% (Max). $^1$H NMR (400 MHz, DMSO-d$^6$): δ 9.80 (s, I 1), 8.61 (d, 0.80 Hz, 1H), 8.45 (d, J=00 FHz, 1H), 7.98 (s, 1H), 7.68 (d, J=9.20 Hz, 1H), 7.37 (s, 2H), 6.76 (d, J=6.00 Hz, 1H), 4.10 (br, 4H), 2.90-2.9$^2$ (m, 8H), 1.18 (t, J=7.20 Hz, 12H). $^{13}$C NMR (100 MHz, DMSO-d$^6$): 156.19, 151.86, 148.46, 145.28, 136.14, 129.79, 128.23, 126.18, 125.87, 124.25, 121.05, 117.36, 101.37, 52.28, 46.31, 9.92.

Example 3: Synthesis of Compound 3

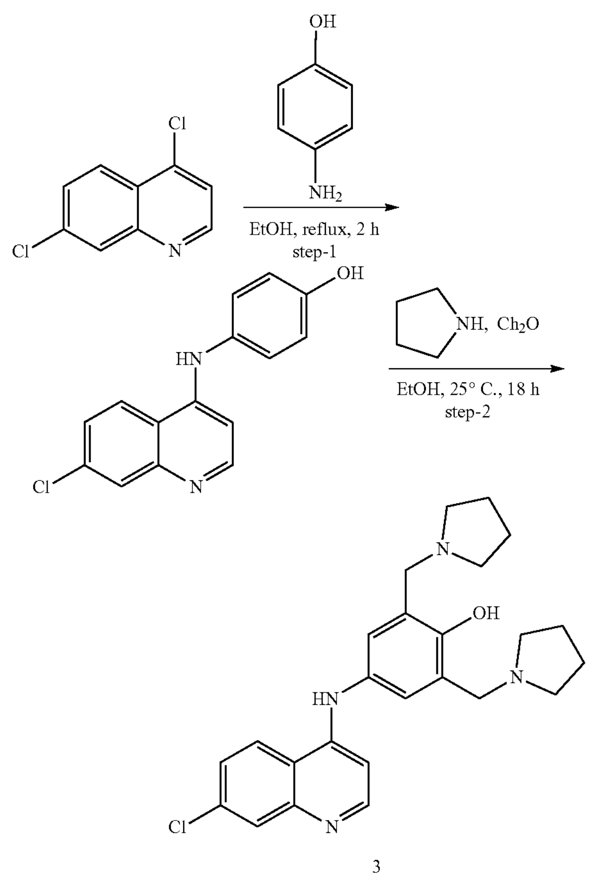

3

Step-1: 4,7-dichloroquinoline (5 g, 25 mmol) and 4-aminophenol (2.75 g, 25 mmol) were refluxed in 125 mL of ethanol for 2 h. The reaction mixture was then cooled to room temperature and the precipitate was removed by filtration and washed successively with a saturated aqueous solution of $NaHCO_3$, water, methanol and then petroleum ether to yield 4-[(7-chloroquinolin-4-yl)amino]phenol as a yellow powder (5.75 g, 84.1%). LCMS: Calculated for $C_{15}H_{11}ClN_2O$ 270.72, Observed 271.1 (M+H), RT. 1.10 min, 99.8% (Max), $^1$H NMR (400 MHz, DMSO-d$^6$): δ 9.59 (s, 1H), 8.52 (d, J=9.20 Hz, 1H), 8.38 (d, J=6.00 Hz, 1H), 7.91 (d, J=2.00 Hz, 1H), 7.61 (dd, J=2.00, 8.80 Hz, 1H), 7.18 (d, J=8.80 Hz, 2H), 6.88 (d, J=8.80 Hz, 2H), 6.56 (d, J=6.00 Hz, 1H).

Step-2: 4-[(7-chloroquinolin-4-yl)amino]phenol (1 g, 3.6 mmol), pyrrolidine (1.1 g, 16 mmol) and 37% aqueous solution of formaldehyde (1.3 mL, 16 mmol) were taken in 5 mL of ethanol and stirred at 25° C. for 18 h. The reaction mixture was then evaporated, and the residue was purified by flash chromatography to afford 3 (0.45 g, 31.1%) as reddish orange solid. LCMS: Calculated for $C_{25}H_{29}ClN_4O$ 436.98, Observed 437.2 (M+H), RT. 2.07 min, 99.2% (Max). HPLC: RT 1.94 min, 98.84% (Max). $^1$H NMR (400 MHz, DMSO-d$^6$): δ 9.04 (s, 1H), 8.40-8.46 (m, 2H), 7.87-7.88 (m, 1H), 7.56 (dd, J=1.96, 9.00 Hz, 2H), 7.26 (s, 2H), 6.73-6.74 (m, 1H), 4.07 (br, 4H, 2.92 (br, 8H), 1.88 (br, 8H). $^{13}$C NMR (100 MHz, DMSO-d$^6$): 154.51, 152.17, 149.57, 134.32, 130.73, 127.74, 126.41, 125.15, 124.96, 121.99, 118.19, 101.42, 54.72, 53.23, 23.45.

Example 4: HEK Cell Assay

Human whole blood from healthy donors was drawn into EDTA Vacutainer tubes and the experiment started within 2 hr of draw. Four parts blood was diluted with 1 part PBS. 10 mM compounds stock solutions were serially diluted 1:3 eleven times in DMSO. Each serial dilution was further diluted by transferring 3 μl to 100 μl RPMI. For the stimulation only and no stimulation controls, 3 μl 100% DMSO was transferred to 100 μl RPMI. Then, 5 μl of each of these dilutions were transferred to 96-well tissue culture grade U-bottom plate in triplicate for each ligand and each donor. Final inhibitor concentrations were 10, 3.3, 1.1, 0.37, 0.12, 0.04, 0.014, 0.0046, 0.0015, 0.00051, 0.00017, 0.00006 μM. No inhibitor (stimulation only) controls were included in triplicate for each donor. Diluted blood was dispensed on top of inhibitor dilutions at 150 μl/well. Plates were incubated at 37° C. 5% $CO_2$ for 30 min. For TLR7 stimulation, 10 mM stock of a TLR7-specific small molecule agonist in DMSO was diluted to 90 μM in RPMI and 5 μl were added to each inhibitor dilution for each donor. Final concentration was 3 μM. For TLR8 stimulation, 10 mM stock of a TLR8-specific small molecule agonist in DMSO was diluted to 15 μM in RPMI and 5 μl were added to each inhibitor dilution for each donor. Final concentration was 0.5 μM. No stimulation controls were included in triplicate for each donor. Plates were incubated at 37° C. 5% $CO_2$ overnight. Next day, plasma was collected and IL-6 was measured by AlphaLISA (PerkinElmer AL223 according to manufacturer's protocol.

Into 384 CulturePlates (Corning 3707) was placed 5000 c/w of HEK293 TLR7/NFKb reporter cells in 30 μL DMEM without phenol red and 10% i.a. FCS and 2 mM L-glutamine. The cells were incubated for 24 h at 37 degrees Celsius, 10% carbon dioxide and 90% relative humidity. 3 μL of controls, standards, and compounds were dispensed to wells, incubated for 30 min then 3 μL of R848 agonist (Resiquimod) in 20 mM HEPES buffer was added. After incubation for 5 hours, it was allowed to stand at room temperature for 15 min. 10 μL of Steady-Glo substrate reagent was added and assay plates were shaken for 5 min at 1500 rpm. The assay plate was allowed to sit for 30 min at room temperature and then read on an EnVision plate reader.

TABLE 1
In Vitro TLR-7 and 8 inhibition
| COMPOUND | STRUCTURE | $IC_{50}$ TLR7 (IL6 READOUT) HEK TRANS-FECTED[B)] | $IC_{50}$ TLR7 (IL6 READOUT) HUMAN WHOLE BLOOD (N = 2)[A)] | $IC^{50}$ TLR8 (IL6 READOUT) HUMAN WHOLE BLOOD (N = 2)[C)] |
|---|---|---|---|---|
| CHLOROQUINE | 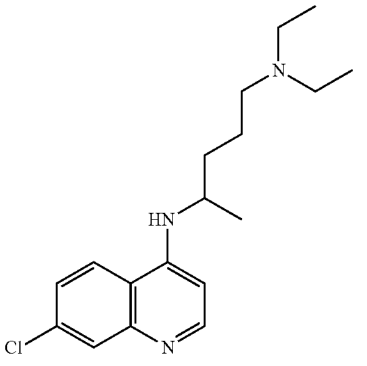 [SMILES: CCN(CC)CCCC(C)Nc1ccnc2cc(Cl)ccc12] | NT | 2.28 μM | 53.3 μM |
| HYDROXY-CHLOROQUINE HCQ | 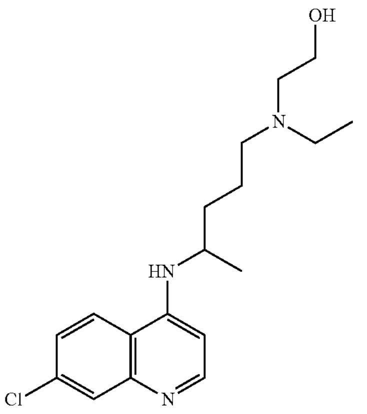 [SMILES: CCN(CCO)CCCC(C)Nc1ccnc2cc(Cl)ccc12] | NT | 0.96 μM | 1.24 μM |
| PYRONARIDINE (I) | 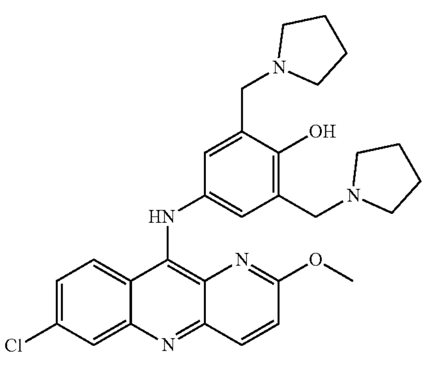 [SMILES: COc1ccc2nc3cc(Cl)ccc3c(Nc3cc(CN4CCCC4)c(O)c(CN4CCCC4)c3)c2n1] | 5.00 μM | 0.21 μM | 0.61 μM |

TABLE 1-continued

| In Vitro TLR-7 and 8 inhibition | | | | |
|---|---|---|---|---|
| COMPOUND | STRUCTURE | $IC_{50}$ TLR7 (IL6 READOUT) HEK TRANS-FECTED[B)] | $IC_{50}$ TLR7 (IL6 READOUT) HUMAN WHOLE BLOOD (N = 2)[A)] | $IC^{50}$ TLR8 (IL6 READOUT) HUMAN WHOLE BLOOD (N = 2)[C)] |
| CYCLOQUINE (II) | 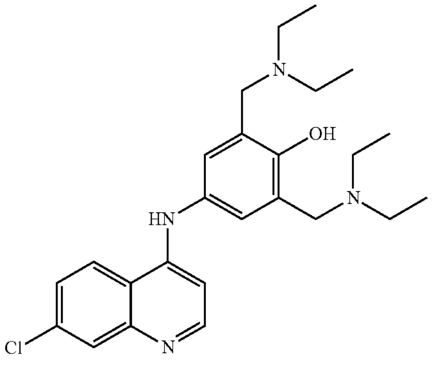 [SMILES: CCN(CC)Cc1cc(Nc2ccnc3cc(Cl)ccc23)cc(CN(CC)CC)c1O] | 1.39 μM | NT | NT |
| BISPYROQUINE (III) | 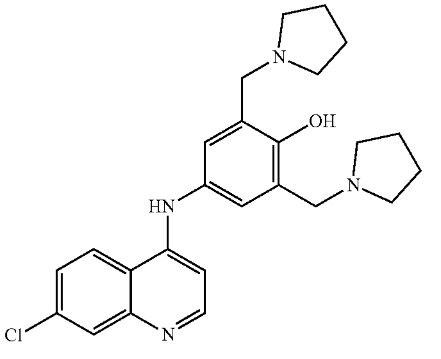 [SMILES: Oc1c(CN2CCCC2)cc(Nc2ccnc3cc(Cl)ccc23)cc1CN1CCCC1] | 4.59 μM | NT | NT |
| AMODIAQUINE | 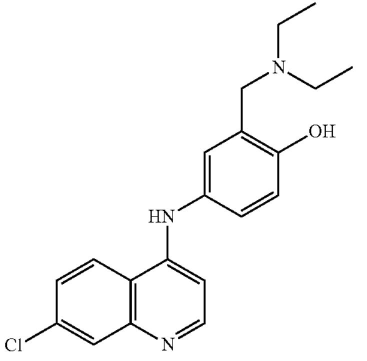 [SMILES: CCN(CC)Cc1cc(Nc2ccnc3cc(Cl)ccc23)ccc1O] | >10 μM | NT | NT |

Results are given in the following table.

A: $IC_{50}$<1 μM

B: $IC_{50}$: 1 μM-20 μM

C: $IC_{50}$>20 μM

TABLE 1

| Compound | Potency |
|---|---|
| 1 | A |
| 2 | A |
| 3 | A |

Example 5: Phenotypic Testing in Biomap Panel

Pyronaridine was profiled in the BioMAP® Diversity PLUS (BioSeek LLC, South San Francisco, CA) panel comprised of a well characterized set of complex primary human cell systems at 10, 3.3, 1.1, and 0.3 μM. Pyronaridine was tested across 12 BioMAP® Systems containing early passage primary human cells cultured alone or as cocultures and stimulated with various proinflammatory or immuno-modulatory stimuli. These systems have been described previously (Xu et al., 2012) and include (primary human cell types/stimuli): 3C [venular endothelial cells (HuVEC)/IL-1, TNF, and IFN], 4H (HuVEC/IL-4 and histamine), LPS (PBMC and HuVEC/LPS), Sag (PBMC and HuVEC/TCR ligands), BT (B cells and PBMC/anti-IgM and low levels of TCR ligands), BE3C (bronchial epithelial cells/IL1, TNF, and IFN), BF4T (bronchial epithelial cells and human dermal fibroblasts/TNF and IL-4), HDF3CGF (human dermal fibroblasts/IL-1, TNF, IFN, epidermal growth factor, basic fibroblast growth factor, and platelet-derived growth factor-BB), KF3CT (keratinocytes and dermal fibroblasts/IL-1, TNF, and IFN), CASM3C (coronary artery smooth muscle cells/ILL-1, TNF, and IFN), MyoF (lung fibroblasts/TNF and transforming growth factor), and Mphg (HuVEC and macrophages/TLR2). A BioMAP activity profile was generated based on the levels of various readout parameters including cytokines or growth factors, expression of surface molecules, and cell proliferation. For more technical details, see (Xu et al. (2012). RN486, a selective Bruton's tyrosine kinase inhibitor, abrogates immune hypersensitivity responses and arthritis in rodents. J. Pharmacol. Exp. Ther. 341, 90-103).

There are 8 common activities that are annotated within the following systems: HDF3CGF (PAI-1, Prolif 72), MyoF (αSMA, VCAM-1, Collagen I, Collagen III, SRB) and IMphg (SRB-M).

There are 38 differentiating activities within the following systems: 3C (TM, uPAR, Prolif), 4H (P-selectin, uPAR), LPS (MCP-1, TM, IL-8, IL-1α, M-CSF, sPGE2, sTNFα), BF4T (Eotaxin 3), BE3C (uPAR, HLA-DR, MMP-9, PAI-1), CASM3C (uPAR, HLA-DR, M-CSF), HDF3CGF (MCP-1, VCAM-1, EGFR, M-CSF, MMP-1, TJMP-1, TIMP-2), KF3CT (MCP-1, MMP-9, PAI-1), MyoF (Collagen IV, IL-8, MMP-1, TIMP-1) and lMphg (MCP-1, E-selectin, CD69, IL-8). Please note, systems with detectable cytotoxicity are excluded from analysis (SAg and BT).

Differentiating biomarkers are defined when one profile has a readout outside of the significance envelope with an effect size >20% (|log 10 ratio|>0.1), and the readout for the other profile is either inside the envelope or in the opposite direction.

Example 6: Mouse Spleenocytes Cell Assay with R848/CpG Stimulation and Inhibition with Antimalarias Mouse spleen from healthy, female C57/BL-6/N mice (n=2) were taken out in 50 mL tubes with B-Cell medium and the experiment started directly. The spleen was grinded through a cell strainer by using the punch of a syringe into a 50 mL Falcon tube. Cell strainer and punch were flushed with appropriate amount of washing buffer to avoid cellloss. Then the spleenocytes were centrifuged for 10 min at 552 xg (1600 rpm), 4° C. The erythrocytes within the cell pellet were lysed by resuspending pellet in iml ACK-lysing buffer (4° C.) and incubate for 1 minute at RT. Lysis was stopped by filling up to 50 ml with washing buffer and centrifuged for 10 min at 552 xg (1600 rpm), 4° C. Cells were washed in B-cell Media (IMDM+25 mM HEPES+10% FCS+pen/strep+NEAA 10 nM+Sodium Pyrovat 100 nM, ß-Mercaptoethanol 50 nM), counted and seeded in a density of 148500 cells per well in a 96 well MTP (135 μl of 1,1×106c/ml). The cells were pre-treated with antimalarials (15 μL, in different concentrations according to dose-response curve ranging from 100 pM-50 μM)) for 30 min, at 37° C., 5% CO2, followed by TLR7/8 stimulation with R848 (15 μl, final concentration of 1 μM) or a TLR9 stimulation with CpG (15 μl, final concentration of 5 μM) and incubated at 37° C., 5% CO2 for 18-24 hours.

Supernatants were collected and transferred into a 96 well round bottom MTP and stored at −20° C. until ELISA formouse IL6 and mouse TNFa were performed. Plates were read directly after assay on an Envision Multiplate reader. Results were analyzed with GraphPadPrism V8.0. Plot the calculated amount of produced IL6 or TNFa in pg/ml on y-axis and the concentration of each MSC concentration at half logarhythmic scaling on the x-axis to achieve a dose-response curve. Determine IC50 values using Graph Pad Prism analysis software (Transform Y values using "X=Log (X) and log inhibitor vs. response; Variable slope (four parameters).

TABLE 2

| Compound | Structure | $IC_{50}$ TLR7/8 (IL6 readout) mouse spleenocytes (n = 2) | $IC_{50}$ TLR7/8 (TNF readout) mouse spleenocytes (n = 2) | $IC_{50}$ TLR9 (IL6 readout) mouse spleenocytes (n = 2) | $IC_{50}$ TLR9 (TNF readout) mouse spleenocytes (n = 2) |
|---|---|---|---|---|---|
| Chloroquin | 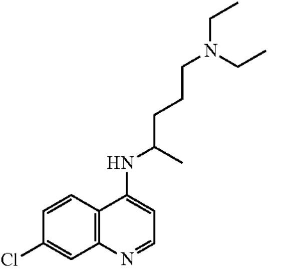 [SMILES: CCN(CC)CCCC(C)Nc1ccnc2cc(Cl)ccc12] | NT | NT | NT | NT |

TABLE 2-continued

| Compound | Structure | $IC_{50}$ TLR7/8 (IL6 readout) mouse spleenocytes (n = 2) | $IC_{50}$ TLR7/8 (TNF readout) mouse spleenocytes (n = 2) | $IC_{50}$ TLR9 (IL6 readout) mouse spleenocytes (n = 2) | $IC_{50}$ TLR9 (TNF readout) mouse spleenocytes (n = 2) |
|---|---|---|---|---|---|
| Hydroxy-chloroquine HCQ | 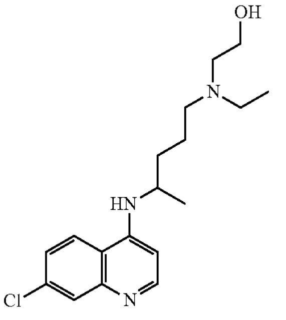 [SMILES: CCN(CCO)CCCC(C)Nc1ccnc2cc(Cl)ccc12] | no suppr<br>27.1 μM | no suppr<br>no suppr | 15.38 μM<br>1.7 μM | no suppr<br>11.48 μM |
| Pyronaridine (I) | 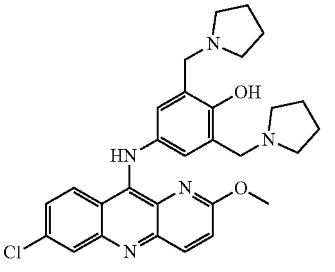 [SMILES: COc1ccc2nc3cc(Cl)ccc3c(Nc3cc(CN4CCCC4)c(O)c(CN4CCCC4)c3)c2n1] | 7.23 μM<br>1.56 μM | 1.75 μM<br>3.74 μM | 0.014 μM<br>0.035 μM | 0.021 μM<br>0.14 μM |

While a number of embodiments of this invention are described herein, it is apparent that the basic examples may be altered to provide other embodiments that utilize the compounds and methods of this invention. Therefore, it will be appreciated that the scope of this invention is to be defined by the appended embodiments rather than by the specific embodiments that have been represented by way of example.

We claim:

1. A method of inhibiting TLR 7 and/or 8 activity in a patient in need thereof, comprising: administering to said patient an effective amount of a compound selected from the group consisting of:

(I)

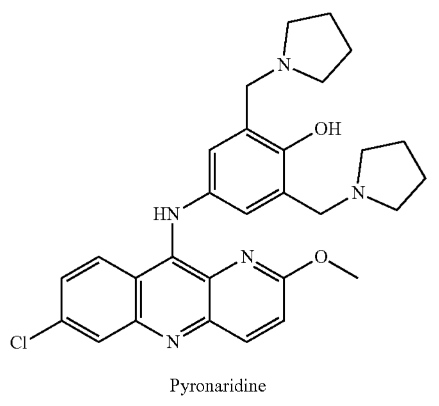

Pyronaridine

-continued (III)

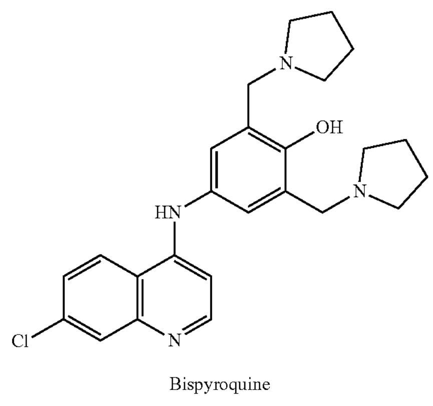

Bispyroquine and/or a pharmaceutically acceptable salt thereof, and wherein the patient in need thereof has a disorder selected from rheumatoid arthritis (RA), psoriatic arthritis, osteoarthritis, systemic lupus erythematosus (SLE), lupus nephritis (LN), ankylosing spondylitis, osteoporosis, systemic sclerosis, multiple sclerosis (MS), psoriasis, type-1 diabetes, type-2 diabetes, inflammatory bowel disorder (IBD), Chrohn's Disease, ulcerative colitis, hyperimmunoqlobulinemia D and periodic fever syndrome, cryopyrin-associated periodic syndromes, Schnitzler's syndrome, systemic juvenile idiopathic arthritis, adult's onset Still's disease, qout, pseudoqout, SAPHO syndrome, Castleman's disease, sepsis, stroke, atherosclerosis, celiac disease, deficiency of IL-1 receptor agonist (DIRA), Alzheimer's disease, and Parkinson's disease.

2. The method of claim 1 wherein the disorder is selected from RA, SLE, LN, and MS.

3. The method of claim 1, wherein the compound is administered in combination with one or more additional active ingredient(s).

4. The method of claim 3, wherein the one or more additional active ingredient(s) is useful to treat autoimmune disorders.

5. The method of claim 4, wherein the one or more additional active ingredient is a corticosteroid.

6. A method for treating a TLR 7 and/or 8-mediated disorder in a patient in need thereof, comprising: administering to said patient a compound selected from the group consisting of:

(I)

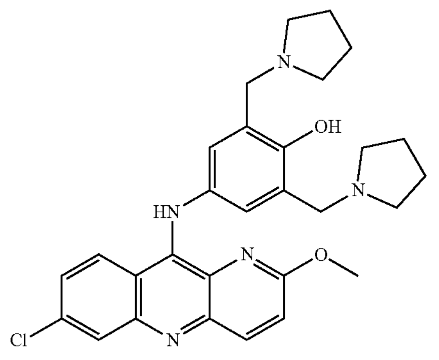

Pyronaridine (III)

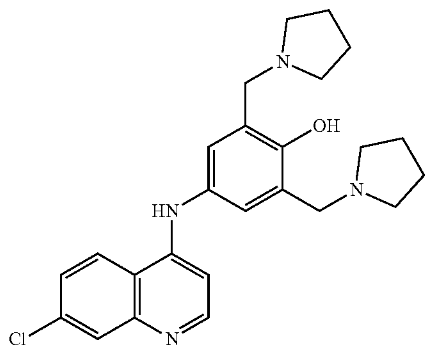

Bispyroquine and/or a pharmaceutically acceptable salt thereof, and wherein the disorder is selected from rheumatoid arthritis (RA), psoriatic arthritis, osteoarthritis, systemic lupus erythematosus (SLE), lupus nephritis (LN), ankylosing spondylitis, osteoporosis, systemic sclerosis, multiple sclerosis (MS), psoriasis, type-1 diabetes, type-2 diabetes, inflammatory bowel disorder (IBD), Chrohn's Disease, ulcerative colitis, hyperimmunoglobulinemia D and periodic fever syndrome, cryopyrin-associated periodic syndromes, Schnitzler's syndrome, systemic juvenile idiopathic arthritis, adult's onset Still's disease, gout, pseudoqout, SAPHO syndrome, Castleman's disease, sepsis, stroke, atherosclerosis, celiac disease, deficiency of IL-1 receptor agonist (DIRA), Alzheimer's disease, and Parkinson's disease.

7. The method of claim 6, wherein the disorder is selected from RA, SLE, LN, and MS.

8. A method of treating a SARS-Co V-1 or SARS-Co V-2 infection in a human subject in need thereof, comprising:

administering an effective amount of a compound selected from the group consisting of:

(I)

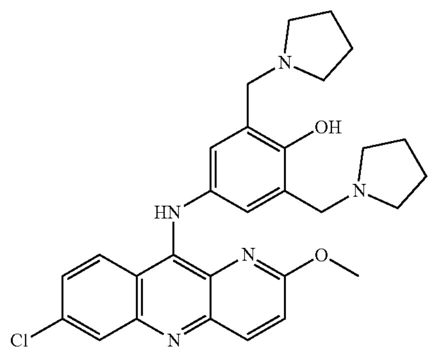

Pyronaridine (II)

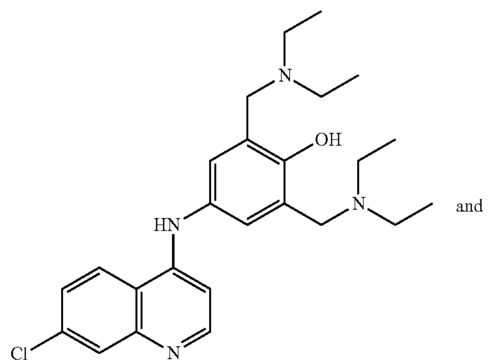

and

Cycloquine (III)

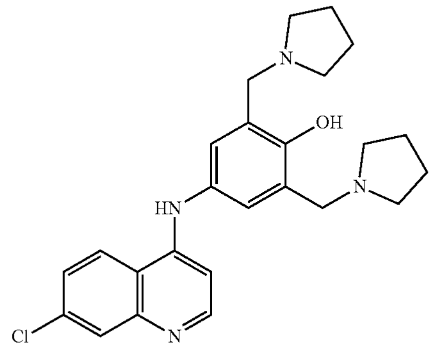

Bispyroquine and/or a pharmaceutically acceptable salt thereof, to said subject.

9. The method of claim 8, further comprising administering an effective amount of one or more additional active ingredients to the subject in need thereof.

10. The method of claim 9 wherein the one or more additional active ingredients is an antiviral agent.

11. The method of claim 10, wherein the antiviral agent is remdesivir.

12. The method of claim 8, wherein the infection is SARS-Co V-2.

13. The method of claim 12, wherein the SARS-Co V-2 causes COVID-19.

* * * * *